United States Patent [19]

Watanabe et al.

[11] Patent Number: 4,730,262

[45] Date of Patent: Mar. 8, 1988

[54] METHOD OF DISPLAYING THE SCANNING SCHEDULE IN A COMPUTER TOMOGRAPHIC APPARATUS

[75] Inventors: Yoshihiko Watanabe; Yoshikazu Ogawa; Akimoto Nakase, all of Musashino, Japan

[73] Assignee: Yokogawa Medical Systems, Limited, Tokyo, Japan

[21] Appl. No.: 789,307

[22] PCT Filed: Jan. 22, 1985

[86] PCT No.: PCT/JP85/00023

§ 371 Date: Sep. 24, 1985

§ 102(e) Date: Sep. 24, 1985

[87] PCT Pub. No.: WO85/03856

PCT Pub. Date: Sep. 12, 1985

[30] Foreign Application Priority Data

Feb. 29, 1984 [JP] Japan ................. 59-29829[U]

[51] Int. Cl.⁴ .................. G01N 23/04; A61B 6/03
[52] U.S. Cl. ................... 364/521; 340/721; 340/754
[58] Field of Search ........... 364/414, 417, 518, 521; 378/98, 99, 100, 4, 16; 340/721, 722, 753, 754

[56] References Cited

U.S. PATENT DOCUMENTS

| | | | |
|---|---|---|---|
| 3,999,094 | 12/1976 | Grim | 378/98 |
| 4,251,729 | 2/1981 | Pfeifer | 378/98 |
| 4,303,973 | 12/1981 | Williamson, Jr. et al. | 340/722 |
| 4,396,977 | 8/1983 | Slater et al. | 340/722 |
| 4,593,355 | 6/1986 | Chase | 364/414 |
| 4,613,949 | 9/1986 | Glover et al. | 364/414 |
| 4,628,444 | 12/1986 | Nozawa et al. | 340/722 |

OTHER PUBLICATIONS

Crooks et al., "Nuclear Magnetic Resonance Whole--Body Image Operating at 3.5U Gauss," *Radiology,* vol. 143, No. 1, Apr. 1982, pp. 169-174.
General Electric Information Card, 5600, copyright 1983.
Jarett, "Using Charts to present International Trade Data," *IEEE Computer Graphies and Application,* vol. 3, No. 9, Dec. 1983, pp. 55-61.
Caporal et al., "Tools for Automated Statistical Graphics," *IEEE Computer Graphics and Application,* vol. 1, No. 4, Oct. 1981, pp. 72-82.

*Primary Examiner*—Errol A. Krass
*Assistant Examiner*—Daniel W. Juffernbruch
*Attorney, Agent, or Firm*—Moonray Kojima

[57] ABSTRACT

A display method in a computer tomographic apparatus is disclosed wherein a plurality of bar graphs representing the scanning schedule are generated on a display. The bar graph depicts the scanning time extending one distance and the margin time extending a second distance at a smaller width. When the scanning is taking place, signals are generated to plot over the scanning bar graph during the scanning time and plot over the margin bar graph during the margin time. The scanning time and margin time bar graphs adjoin one another and are distinguishable by the margin time extending from the scanning bar at a narrower width. This configuration allows an operator to readily determine at a glance the scanning step and progress thereof.

4 Claims, 5 Drawing Figures

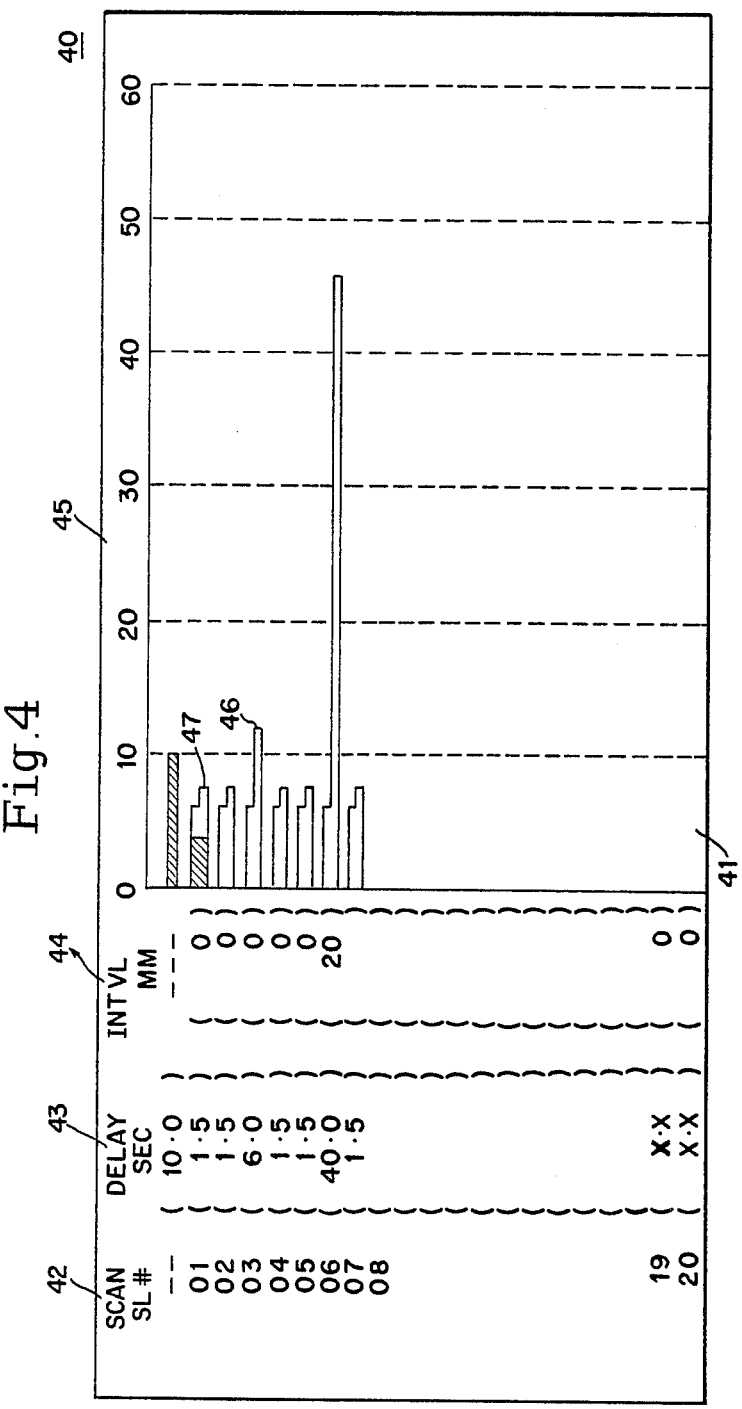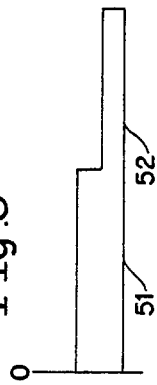

METHOD OF DISPLAYING THE SCANNING SCHEDULE IN A COMPUTER TOMOGRAPHIC APPARATUS

DESCRIPTION

1. Technical Field

This invention concerns a method of displaying the setting state of the scanning schedule and the proceeding state of the scanning schedule in a computer tomographic apparatus utilizing X-ray or nuclear magnetic resonance or the like.

2. Background Art

In the computer tomographic apparatus utilizing X-ray, nuclear magnetic resonance or the like, a plurality of images are photographed continuously depending on the case by conducting a series of plurality scannings. In this case, a schedule such as the margin time from the completion of the previous scanning to the start of the next scanning, the displacing amount of the scanning position (for example, moving amount of a patient table) or the like is previously set on every one scanning, and a series of plurality scannings is carried out in accordance with the schedule after the start of the scanning (hereinafter referred to as the schedule scanning).

In the conventional apparatus, CRT or like other screen is used, and the setting for the scanning schedule is effected in a dialog system utilizing letters, while the proceeding state of the scanning schedule is also effected by letters. Accordingly, it is inconvenient to quickly at a glance understand the setting state and the proceeding state of the scanning schedule.

DISCLOSURE OF INVENTION

The object of this invention is to provide a display method for use in a computer tomographic apparatus in which the setting state for the schedule of a plurality of scanning and the proceeding state thereof are displayed so that they can be understood quickly at a glance.

In order to attain the foregoing object, according to this invention, the sum of the length for the scanning time and the length of the margin time till the start of the next scanning is displayed as a graph using a graphic figure for each of the plurality of scannings, and the configuration is made different between the portion for expressing the scanning time and the portion for expressing the margin time, as well as the display configuration is also made different between the executed and not-executed portions for the schedule in each of the graphs.

BRIEF DESCRIPTION OF DRAWINGS

FIG. 4 is a schematic view showing the displayed images by the embodied apparatus according to this invention, and FIG. 5 is an enlarged view for a portion of FIG. 4.

BEST MODE FOR CARRYING OUT THE INVENTION

Figure 1:
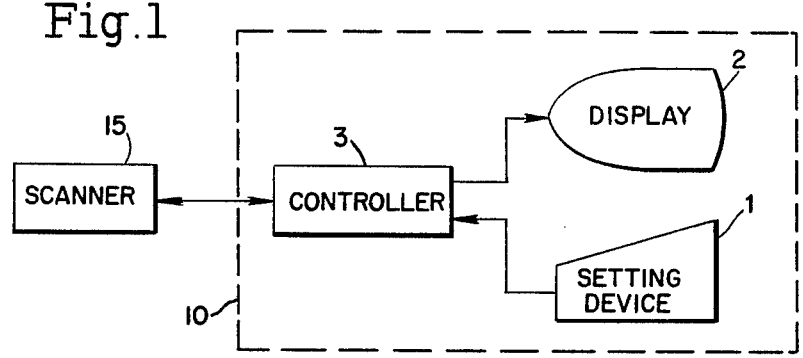
FIG. 1 is a constitutional block diagram showing the constitution of one embodied apparatus according to this invention.

At first, explanation is made for the constitution of the embodied apparatus according to this invention referring to FIG. 1. The embodied apparatus 10 comprises a setting device 1, a display 2 and a controller 3 so as to control a scanner 15. In the embodied apparatus 10, a push button switch and an alpha numeric keyboard are used as the setting device 1, a CRT display is used as the display 2 and a computer is used as the controller. The output of the setting device 1 is connected to the first input of the controller 3, the first output of the controller 3 is connected to the display 2 and the second input and the output of the controller 3 are connected respectively to the output and the input of the scanner 15.

Figure 2:
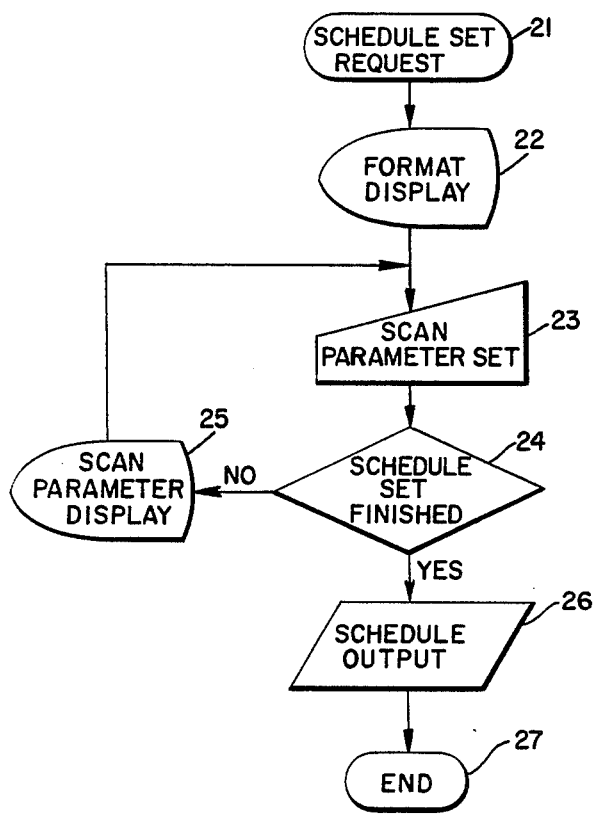
FIG. 2 is a flow chart for explanating the method of setting and displaying the scanning schedule in the embodied apparatus according to this invention.
Figure 3:
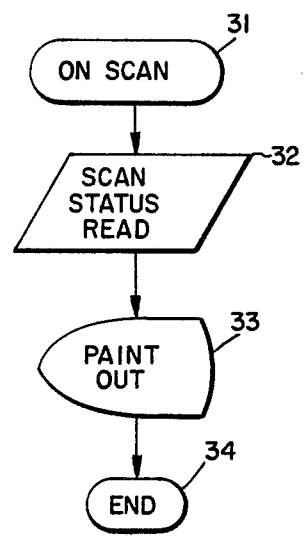
FIG. 3 is a flow chart illustrating the method of tracing and displaying the proceeding state of the scanning schedule in the embodied apparatus according to this invention.

Then, explanation will be made for the method of displaying the setting state and the proceeding state of the scanning schedule in the embodied apparatus referring to the drawings. In addition to FIG. 1, FIG. 2 through FIG. 5 are also used for the explanation. FIG. 2 is a flow chart which explains the method of setting and displaying the scanning schedule in this apparatus, FIG. 3 is a flow chart which explains the method of tracing and displaying the proceeding state of the scanning schedule in the apparatus, FIG. 4 shows a format image 41 on a display screen 40 of the display 2 and FIG. 5 shows a portion 47 of displayed images in an enlarged scale.

At first, when the scanning schedule setting has been demanded through the setting device 1 from an operator (processing 21 in FIG. 2), an image signal corresponding to the format image 41 is formed in the controller 3 to which a signal corresponding to the request is inputted, and the format image 41 is displayed by the image signal on the screen 40 of the display 2 (procession 22 in FIG. 2). As shown in FIG. 4, the format image 41 displays letters: SCAN SL # at the position 42, letters: DELAY SEC at the position 43, letters: INTVL MM at the position 44, as well as numericals of 0, 10, 20, 30, 40, 50 and 60 at the position 45 and scales indicated by fat lines and broken lines respectively. SCAN SL # is a name for the column in which the numbers for the individual scannings in the series of plurality scannings are displayed. DELAY SEC indicates the name of a column in which the margin time up to the start of the next scanning is displayed by numericals and the unit of time. INTVL MM is a name for the column in which the moving amount of the scanning position is displayed by numericals and the unit of the distance. The numericals and the scales at the position 45 indicate the scales of the plane on the graph in which the scanning time and the margin time for the individual scannings are displayed by a graph using a band-like graphic figure, that is, a bar graph.

Then, when the margin time and the scanning position moving amount are set sequentially on every individual scannings by the operator through the setting device 1 (procession 23 in FIG. 2), the control operation of the controller 3 displays numericals indicating the scanning order in the column shown at the position 42, numericals indicating the margin time for the second unit in the column shown at the position 43, the moving amount of the scanning position by mm unit in the column shown at the position 44 and the bar graph for the scanning time and the margin time for individual scannings on the plane of the graph shown at the position 45 respectively in the format image 41 (procession 25 in FIG. 2). As shown for example, in FIG. 5, the bar graph 46 respresents the scanning time as a broad width band-like graphic figure and displays the margin time as a narrow width band-like graphic figure 52. The length of the band is indicated by the time of second unit. The scanning time is a predetermined constant value inherent to the scanning device 15.

When the scanning schedule is displayed by the arrangement of such a plurality of bar graphs, the setting state of the scanning schedule can be understood at a glance.

When such a setting has been completed for all of the scannings in one schedule (procession 24 in FIG. 2), the set scanning conditions are applied under the control of the controller 3 to the scanner 15 (procession 26 in FIG. 2), and the setting for the scanning schedule is completed (procession 27 in FIG. 2).

Then, when the scanner 15 starts the scanning, the procedures as shown in FIG. 3 is conducted by the controller 3, for example, on every 0.5 sec, a signal indicating the scanning state is read from a scanner 15 (procession 32 in FIG. 3) and then, depending on the signal, the band-like graphic form in the display 2 relevant to the scanning now in execution is painted out for a length corresponding to (0.5 sec) (procession 33 in FIG. 3). The procedures are repeated during effecting of the scanning schedule, in which the painting out of the band-like graphic figure 47 is advanced.

This state is shown by the hatched bar graph in FIG. 4.

In this way, since the bar graphs are painted out along with the advance of the scanning schedule, the proceeding state of the scanning schedule can be understood at a glance based on the proceeding state of the painting out. With the completion of the scanning schedule, painting out for all of the bar graphs is completed.

Although the portion of the bar graph that has already been executed is painted out while the not yet executed portion is left blank, the mode may be reversed.

In the embodied apparatus, although the display for the moving state of the table is not carried out but it can optionally be displayed by the bar graph in the same manner depending on the requirement.

As the display, color CRT, liquid crystal display, plasma display or the like can also be used as well as the monochrome CRT.

Furthermore, the scanning time and the margin time may be distinguished not necessarily by to the width of the bar graph, but also by using two modes capable of distinguishig from each other. It is the same for the display of the proceeding state of the scanning schedule, the change in the color or the brilliancy may also be utilized not always restricted only to the painting out.

The foregoings show one embodiment of this invention in which the scanning schedule is displaced by the bar graph using the band-like graphic figure, but the graph is not restricted to the bar graph but an appropriate graph may be used depending on the requirement, for example, a circular graph using a fan-like graphic figure.

INDUSTRIAL APPLICABILITY

As described above, the setting state of the scanning schedule and the proceeding state thereof in the computer tomographic apparatus can be displayed according to this invention such that it can be understood quickly at a glance. Accordingly, since the user of the computer tomographic apparatus can concentrate his attention upon the patient, there is an advantage of improved diagnostic efficiency.

What is claimed is:

1. A method of displaying the scanning schedule for computer tomographic apparatus comprising a scanner for scanning an object to be examined; a setting device for setting the scanning schedule including a margin time setting value between a previous scanning step and the next scanning step for each of a series of a plurality of scanning steps to be effected by said scanner; a visual display for concurrently displaying a schedule of scannings as numbers, delay times as numbers, intervals as numbers and graphic figures representing the scanning schedule; and a controller for causing said scanner to conduct scanning for the object according to the schedule for a series of a plurality of scanning steps set by the setting device, and displaying as graphic figures the set scanning schedule and proceeding state of the scanning schedule on said display; said method comprising the steps of displaying the individual scanning steps in the visual display as a first bar representing the length of the scanning time and a second bar having a different configuration from said first bar and added as an extension of the first bar for indicating the length of time of said margin time, with the first and second bars being disposed on said visual display opposite the corresponding step of the scanning schedule, delay time and interval; and changing in real time the composition of the first bar as the scanning proceeds until the scanning in that step is completed and then subsequently changing in real time the composition of the second bar as the margin time proceeds, whereby an operator can determine instantaneously from the number of the scanning schedule, the number of the delay, and from the number of the interval, and the composition of the first and second bars in the visual display, the steps already executed, the exact part of the exact step of the scanning schedule being executed, and the steps still to be executed.

2. The method of claim 1, wherein the width of said first bar is wider than the width of the second bar, and wherein the portion of the first bar corresponding to the executed schedule is changed to be either a painted out portion or a blank portion, and the other portion of the first bar corresponding to the not yet executed schedule remains the other of the painted out portion or blank portion.

3. The method of claim 1, wherein the portion of the first bar corresponding to the executed schedule is displayed by either one of two colors and the other portion of the first bar corresponding to the not yet executed schedule remains displayed by the other color.

4. The method of claim 1, wherein the portion of the first bar corresponding to the executed schedule is displayed by either one of two brilliance levels and the other portion of the first bar corresponding to the not yet executed schedule is displayed by the other brilliance level.

* * * * *